United States Patent [19]

ElSohly et al.

[11] Patent Number: 5,036,014
[45] Date of Patent: Jul. 30, 1991

[54] DEUTERATED CANNABINOIDS AS STANDARDS FOR THE ANALYSIS OF TETRAHYDROCANNABINOL AND ITS METABOLITES IN BIOLOGICAL FLUIDS

[76] Inventors: Mahmoud A. ElSohly, 41 Shelia Dr.; Thomas L. Little, Jr., P.O. Box 1737, both of Oxford, Miss. 38655

[21] Appl. No.: 306,292

[22] Filed: Jan. 31, 1989

[51] Int. Cl.$^5$ ............................................. G01N 24/00
[52] U.S. Cl. ........................................ 436/8; 436/16; 436/92; 436/173; 436/816; 436/825; 436/901
[58] Field of Search ................................. 436/8–18, 436/161, 173, 177, 175, 536, 804, 805, 816, 825, 901, 92

[56] References Cited

U.S. PATENT DOCUMENTS

| 3,966,764 | 6/1976 | Goldstein et al. | 436/92 |
| 4,205,952 | 6/1980 | Cais | 436/536 |
| 4,843,020 | 6/1989 | Woodford | 436/536 |

OTHER PUBLICATIONS

"Standards and Controls", Sigma Product Catalog, p. 1698, 1988.

*Primary Examiner*—David L. Lacey
*Assistant Examiner*—David Redding
*Attorney, Agent, or Firm*—William D. Stokes

[57] ABSTRACT

New internal standards for use in gas chromatography/mass spectrometry test methods, comprising deuterated cannabinoids, have been developed for the analysis of tetrahydrocannabinol and its metabolites in biological fluids.

8 Claims, No Drawings

DEUTERATED CANNABINOIDS AS STANDARDS FOR THE ANALYSIS OF TETRAHYDROCANNABINOL AND ITS METABOLITES IN BIOLOGICAL FLUIDS

BRIEF DESCRIPTION OF INVENTION

This invention is directed to new compounds and compositions that are particularly and uniquely useful as internal standards in the analysis of tetrahydrocannabinol and its metabolites in biological fluids. These new standards have essentially the same partitioning, chromatographic and derivatizing behavior as the compounds to be analyzed.

BACKGROUND OF THE INVENTION

Tetrahydrocannabinol (Delta-9-THC) is the major psychologically active component in the Cannabis plant (marijuana). Administration or use of marijuana or other products of the Cannabis plant, such as hashish and hash oil, can be detected through the analysis of biological fluids, such as blood or urine, for the parent compound delta-9-THC or its major urinary metabolite, namely, 11-nor-delta-9-tetrahydrocannabinol-9-carboxylic acid (THC-COOH). Many different methods have been developed for the analysis of these compounds. Immunoassays are the most widely used today as discussed in the following publications:

Cook, C. E.; Radioimmunoassay of cannabinoids, IN: *Cannabinoid Analysis in Physiological Fluids*, ACS Symposium Series 98, Vinson, J. A., Ed., American Chemical Society, Washington, D.C., 137-154, 1979.

Teale, J. D.; Forman, E. J.; King, L. J.; and Marks, V.; Radioimmunoassay of cannabinoids in blood and urine, *Lancet*, 2:553-555, 1974.

Chase, A. R., Kelley, P. R., Taunton Rigby, A.; Jones, R. T.; and Harwood, T.; Quantitation of cannabinoids in biological fluids by radioimmunoassay, IN: *Cannabinoid Assays in Humans*, NIDA Research Monograph, No. 7, Willette, R. E., Ed., U.S. Department of Health, Education, and Welfare, Washington, D.C., 1-9, 1976.

Jones, A. B.; ElSohly, H. N.; and ElSohly, M. A.; Analysis of the major metabolites of delta-9-tetrahydrocannabinol in urine, V. Cross reactivity of selected compounds in a radioimmunoassay, *J. Anal. Toxicol.*, 8:252-254, 1984.

Rowley, G. L.; Armstrong, T. A.; Crowl, C. P.; Eimstad, W. M.; Hu, W. M.; Kam, J. K.; Rodgers, R.; Ronald, R. C.; Rubenstein, K. E.; Sheldon, B. G.; and Ullman, E. F.; Determination of THC and its metabolites by EMIT homogenous enzyme immunoassay: A summary report, IN: *Cannabinoid Assays in Humans*, NIDA Research Monograph, No. 7, Willette, R. E., Ed., U.S. Department of Health, Education, and Welfare, Washington, D.C., 28-32, 1976.

Rodgers, R.; Crowl, C. P.; Eimstad, W. M.; Hu, M. W.; Kam, J. K.; Ronald, R. C.; Rowley, G. L.; and Ullman, E. F.; Homogenous enzyme immunoassay for cannabinoids in urine, *Clin. Chem.*, 24:95-100, 1978.

However, in the performance of the above noted methods, especially in the forensic setting, it is recommended that they be conducted in conjunction with a confirmatory test based upon a different principle. The confirmatory test found most acceptable in the scientific community is gas chromatography/mass spectrometry (GC/MS). GC/MS is used not only to confirm the presence of the drug in the biological specimen, but also to quantitate the amount of the drug, as, for example, set forth in the following publications:

Nordqvist, M.; Lindgren, J. E.; and Augurell, S.; A method for the identification of acid metabolites of tetrahydrocannabinol (THC) by massfragmentography, IN: *Cannabinoid Assays in Humans*, NIDA Research Monograph, No. 7, Willette, R. E., Ed., U.S. Department of Health, Education, and Welfare, Washington, D.C., 64-69, 1976.

Karlsson, L.; Jonsson, J.; Aberg, K.; and Roos, C.; Determination of delta-9-tetrahydrocannabinol-11-oic acid in urine as its pentafluoropropyl-, pentafluoropropionyl derivative by GC/MS utilizing negative ion chemical ionization, *J. Anal. Toxicol.*, 7:198-202, 1983.

Foltz, R. L.; McGinnis, K. M.; and Chinn, D. M.; Quantitative measurement of delta-9-tetrahydrocannabinol and two major metabolites in physiological specimens using capillary column gas chromatography negative ion chemical ionization mass spectrometry, *Biomed. Mass Spectrom.*, 10:316-323, 1983.

ElSohly, M. A.; ElSohly, H. N.; Stanford, D. F.; Evans, M. G.; and Jones, A. B.; Analysis of human urine for 11-nor-delta-9-tetrahydrocannabinol-9-carboxylic acid: A comparison between HPLC, GC/ECD, GC/FID, and GC/MS methods, IN: *Marijuana '84 Proceedings* of the Oxford Symposium on Cannabis, Harvey, D. J., Ed., IRL Press, Oxtord, England, 137-146, 1985.

Internal standards most suitable for the GC/MS analysis are the deuterated derivatives of the drugs to be analyzed. The deuterated compound currently available for the analysis of THC-COOH is the trideuterated derivative, $d_3$-delta-9-THC-COOH. However, the employment of the trideuterated delta-9-THC-COOH presents several problems. First, this material is rather expensive and is not readily available. Second, the base peak in the mass spectrum of the deuterated standard, most commonly used as the methyl derivative, is at m/z 316 as compared to 313 for the natural metabolite. There is, however, a peak in the mass spectrum of the natural metabolite at m/z 316 as a result of a different fragmentation mechanism (through loss of $-(CH_2)_4$ from the side chain) which represents 4-5% of the base peak. Because the natural and deuterated acids are not chromatographically separable, this contribution to the 316 ion of the internal standard (I.S.) from the natural metabolite disturbs the ion ratios for the I.S. and adversely affects the quantitation. This is particularly true at higher concentrations of the natural metabolite.

The subject of this invention is the development of new internal standards which have essentially the same partitioning, chromatographic, and derivatizing behavior as do the compounds to be analyzed. Examples of these compounds include (a) hexadeutero-11-nor-delta-8-tetra-hydrocannabinol-9-carboxylic acid ($d_6$-delta-8-THC-COOH) for use as a internal standard for the analysis of THC-COOH, (b) nonadeutero-delta-9-tetrahydrocannabinol ($d_9$-delta-9-THC), (c) nonadeutero-delta-8-tetrahydrocannabinol ($d_9$-delta-8-THC), and (d) hexadeutero-delta-8-tetrahydrocannabinol ($d_6$-delta-8-THC). The latter three compounds have been developed for use as internal standards for the analysis of delta-9-THC in biological fluids.

DETAILED DESCRIPTION OF THE INVENTION

The compounds of this invention are represented by the formula:

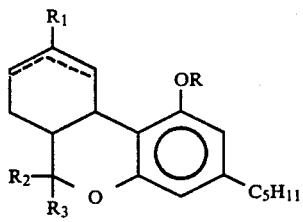

wherein (1) $R_1=CH_3$ and $R_2=R_3=C^2H_3$ or (2) where $R_1=R_2=R_3=C^2H_3$ or (3) wherein $R_1=CH_2OH$, or $C^2H_2OH$ or COOH and $R_2$ and $R_3=C^2H_3$. R may be H or derivatized with an acyl or alkyl moiety such that acyl is of the formula $R_4CO$ and $R_4$ is alkyl having 1-8 carbon atoms, and the alkyl moiety may also have 1-8 C atoms. The bouble bond is between the 8 and 9 positions or between the 9 and 10 positions.

These compounds may be formulated in chemically or pharmaceutically acceptable vehicles or carriers such as water, saline, alcohols, acetone and other organic solvents.

EXAMPLE 1

Synthesis of d6-11-nor-delta-8-Tetrahydrocannabinol-9-Carboxylic Acid dl-6a,7-Dihydro-1-hydroxy-6,6-d6-dimethyl-3-pentyl-6H-dibenzo[b,d]pyran-9(8H)-one(II). Two grams of the lactone (I) was prepared according to the procedure described by Fahrenholtz et al. The total synthesis of dl-delta-9-tetrahydrocannabinol and four of its isomers., *J. American Chem. Soc.* 89; 5934, 1967 was suspended in 75 mL dry anhydrous ether with stirring. A 5 molar equivalent of d3-methyl magnesium iodide was then added over a 15-minute period. After refluxing for 24 hours, the reaction mixture was cooled in an ice bath and 100 mL of 6N HCl was carefully added followed by 100 mL of diethyl ether. After stirring vigorously for 1 hour, the ether layer was washed once with $H_2O$ and once with 5% $NaHCO_3$. After drying with $Na_2SO_4$ the ether layer was concentrated to about 20 mL on rotary evaporator at which time a pale yellow solid precipitated. The resulting precipitate was filtered, washed with ice cold diethyl ether, and then dried yielding 1.25 grams (67%) of II pure enough to proceed to the next step.

dl-6a(beta),7,10,10a(alpha)-Tetrahydro-1-hydroxy-6,6-d6-dimethyl-3-pentyl-6H-dibenzo[b,d]pyran-9(8H)-one (III). To a solution of 100 mL of liquid $NH_3$ and 125 mg of lithium metal is added 1.0 gram of II in 25 mL dry THF with stirring. Whenever the blue color of the reaction mixture began to fade, addition of II was stopped and more lithium metal added. This was continued until a permanent blue color persisted for 5 minutes. Solid $NH_4Cl$ was then added in small portions until the blue color was removed.

The reaction mixture was then brought to room temperature and the liquid $NH_3$ was allowed to evaporate over night. The residue was then stirred vigorously with 100 mL diethyl ether and 100 mL 1N HCl. The ether layer was then washed with 50 mL $H_2O$, dried over $Na_2SO_4$ and evaporated. The product was purified using column chromatography with ether/hexane (30:70) as the mobile phase. The column fractions containing the product were then combined and concentrated in vacuo leaving 0.57 gram (57%) of III as a white solid.

dl-6a(beta),7,10,10a(alpha)-Tetrahydro-1-hydroxy-6,6-d6-dimethyl-3-pentyl-6H-dibenzo[b,d]pyran-9(8H)-one Acetate (IV). 1.0 gram of III is dissolved in 10 mL anhydrous pyridine and 40 mL acetic anhydride with stirring. The reaction mixture is stirred 16 hours at which time it is poured over 100 grams of ice. The aqueous phase was then extracted 3 times with 100 mL of hexane. The hexane layer was then dried over $Na_2SO_4$ and evaporated leaving 1.1 grams (97%) of IV as a pale yellow solid which was pure enough to proceed to the next step.

dl-9-Cyano-6a(beta),7,10,10a(alpha)-tetrahydro-6,6-d6-dimethyl-3-pentyl-6H-dibenzo[b,d]pyran-1-ol Acetate (V). 1.0 gram of IV is dissolved in 50 mL anhydrous benzene with stirring. A catalytic amount of ZnI (approximately 20 mg) is added followed by a 2 molar equivalent of trimethylsilyl cyanide. The reaction mixture is stirred for 2 hours at room temperature at which time 20 mL of methanolic HCl was added. After 1 hour the reaction mixture is evaporated in vacuo and the residue dissolved in 200 mL of ether. The ether layer is extracted with $2\times 50$ mL $H_2O$, dried over $Na_2SO_4$, and evaporated leaving 1.05 grams of the cyanohydrin as an oil. The cyanohydrin is dissolved in 30 mL anhydrous pyridine, and 1.1 molar equivalents of phosphorus oxychloride is slowly added and the mixture refluxed under a nitrogen atmosphere for 30 minutes. After cooling the reaction is poured into 150 mL diethyl ether which is then extracted with 100 mL 2N HCl, 100 mL $H_2O$ dried over $Na_2SO_4$ and evaporated. The product is then purified using column chromatography with ether/hexane (30:70) as the mobile phase. The column fractions containing the product were combined and evaporated leaving 0.8 gram (77%) of V as a white solid.

dl-9-Carboxy-6a(beta),7,10,10a(alpha)-tetrahydro-6,6-d6-dimethyl-3-pentyl-6H-dibenzo[b,d]pyran-1-ol (VI). 0.4 gram of V is dissolved in 50 mL ethanol followed by the addition of 2 mL 50% NaOH. This mixture is then refluxed under a nitrogen atmosphere with stirring for 16 hours. After cooling the reaction mixture is poured into 100 mL $H_2O$, acidified with 6N HCl and extracted with $2\times 150$ mL ether. The organic layers are combined, extracted with 100 mL $H_2O$, dried over $Na_2SO_4$, and evaporated. The residue is recrystallized with $CCl_4$ yielding 0.38 grams (93%) of d6-11-nor-delta-8-tetrahydrocannabinol-9-carboxylic acid (VI) as an off white solid.

EXAMPLE 2

Synthesis of d9-delta-8-Tetrahydrocannabinol dl-6a(beta),7,10,10a(alpha)-Tetrahydro-6,6,9-d9-trimethyl-3-pentyl-6H-dibenzo[b,d]pyran-1-ol(dl-d9-delta-8-tetrahydrocannabinol (VII). 120 mg of the ketone (IV), prepared as previously described in Example 1, is dissolved in 30 mL anhydrous diethyl ether with stirring. 3 molar equivalents of d3-methylmagnesium iodide is then carefully added and the reaction mixture is stirred at room temperature for 6 hours. 20 mL of 1N HCl is then carefully added with stirring continuing for an additional 5 minutes. The ether layer is then washed with 30 mL $H_2O$, dried over $Na_2SO_4$ and evaporated leaving a pale yellow oil containing a mixture of the two isomeric carbinols. The carbinols are then dissolved in 30 mL of benzene containing approximately 10 mg of para toluene sulfonic acid and refluxed under a nitrogen atmosphere for 1 hour. The reaction mixture is then cooled and partitioned with 20 mL of 5% sodium bicarbonate. The organic layer is dried over $Na_2SO_4$ and evaporated in vacuo. The product is then purified using column chromatography with ether hexane (10:90) as the mobile phase. The column fractions containing the product are combined and evaporated leaving 85 mg (80%) of VII as a pale yellow oil.

EXAMPLE 3

Synthesis of $d_6$-delta-8-Tetrahydrocannabinol dl-6a(beta),7,10,10a(alpha)-Tetrahydro-6,6-$d_6$-9-trimethyl-3-pentyl-6H-dibenzo[b,d]pyrano-1-ol(dl-$d_6$-delta-8-tetrahydrocannabinol) (VIII). The title compound is prepared in an identical manner as compound VII except methylmagnesium iodide is substituted for $d_3$-methylmagnesium iodide and was separated as a pale yellow oil.

EXAMPLE 4

Synthesis of $d_9$-delta-9-Tetrahydrocannabinol dl-6a(beta),7,8,10a(alpha)-Tetrahydro-6,6,9-$d_9$-trimethyl-3-pentyl-6H-dibenzo[b,d]pyran-1-ol(dl-$d_9$-delta-9-tetrahydrocannabinol) (IX). 500 mg of VII is dissolved in 50 mL $CHCl_3$ containing 50 mg anhydrous $ZnCl_2$ with stirring at 0° C. HCl gas is then bubbled through the reaction mixture for 30 minutes at which time it is poured into 300 mL anhydrous diethyl ether. The ether chloroform mixture is then washed several times with 50 mL $H_2O$, dried over $Na_2SO_4$ and evaporated in vacuo leaving an oily residue of 9-chloro-$d_9$-hexahydrocannabinol. This material is then dissolved in 50 mL anhydrous toluene, 2.5 molar equivalents of potassium-t-amylate is then added with stirring and the reaction mixture refluxed for 1 hour under a nitrogen atmosphere. After cooling the reaction mixture is poured into ice cold dilute HCl. The organic layer is washed with $H_2O$, dried over $Na_2SO_4$ and evaporated in vacuo. The product is then purified by careful column chromatography using ether/hexane (10:90) as the mobile phase. The column fractions containing the product are combined and evaporated leaving 350 mg (70%) of IX as a pale yellow oil.

EXAMPLE 5

Determination of the concentration of free 11-nor-delta-9-THC-9-carboxylic acid (delta-9-THC-COOH) in urine using $d_6$-delta-8-THC-COOH as internal standard Delta-9-THC-COOH exists either free or conjugated as its glucuronide. Analysis of urine or blood samples for delta-9-THC-COOH is used as an indicator of prior ingestion of marijuana by the individual being tested.

An aliquot (8 mL) of the urine specimen to be tested is mixed with 40 μl of a methanolic solution of $d_6$-delta-8-THC-COOH containing 10 μg/mL. Aliquots of standards and control (8 mL of each) are prepared by spiking blank (negative) urine with various levels of delta-9-THC-COOH are also mixed with 40 μl of the internal standard solution. The aliquots are then made acidic with 1N HCl (pH 3-4) and then extracted with a mixture of hexane/ethyl acetate (9:1). The organic extract is then evaporated to dryness and the residue is converted to the methyl derivatives using tetramethylammonium hydroxide in DSMO and methyl iodide. After acidification of the reaction mixture the methyl derivatives are extracted with iso-octane and the solvent is evaporated. The residue in each tube is then reconstituted in 20 μl of iso-octane and analyzed by gas chromatography/mass spectrometry (GC/MS).

The following are typical conditions for the GC/MS analysis:

Instrument: HP5890 GC interfaced with a HP 5970B MSD;
Column: 15M×0.25 mm DB-1 Capillary Column;
Carrier Gas: Helium at 33Cm/sec. linear velocity;
Oven Temperature: 250° C. isothermal;
Ions to be Monitored: For delta-9-THC-COOH the ions at m/- 372,357 and 313 are monitored while ions at m/- 378,322 and 248 are monitored for the internal standard. Ion ratios for 372/313 and 357/313 are used for identification of the drug in the samples as compared to those in the standards and controls. Ion ratios for 378/248 and 322/248 are used to identify the internal standard. The relative retention time of the delta-9-THC-COOH to the internal standard under these conditions is 1.02.

Calculation of the concentration of the delta-9-THC-COOH in a given sample is carried out by calculating the peak area ratio for the ions at m/- 313/248 and dividing this ratio by the ratio obtained from a standard sample spiked with a known concentration of delta-9-THC-COOH. The resulting number is then multiplied by the concentration of delta-9-THC-COOH in the standard sample to get the concentration of delta-9-THC-COOH in the specimen in question.

If multiple standards are used, a calibration curve can be established and the concentration of the drug in the unknown specimen can be determined from the curve.

EXAMPLE 6

Determination of the total (free and conjugated) concentration of delta-9-THC-COOH in urine employing $d_6$-delta-8-THC-COOH as internal standard The same procedure as described in Example 5 is followed except that the specimens are base hydrolyzed using 1 mL of 10N KOH for 15 minutes at room temperature prior to acidification and extraction.

EXAMPLE 7

Determination of the total (free and conjugated) concentration of delta-9-THC-COOH in blood using $d_6$-delta-8-THC-COOH as internal standard The same procedure as set forth in Example 6 is employed except that smaller volumes of blood (usually 1-2 mL) are used and that the proteins in the blood are first precipitated with an equal volume of acetonitrile. The internal standard ($d_6$-delta-8-THC-COOH) is conveniently added in the acetonitrile and the precipitate centrifuged. The supernatant is transferred to another tube and the precipitate is resuspended in 1 mL acetonitrile followed by centrifugation. The supernatant is then combined with the first extract followed by evaporation of most of the acetonitrile. For hydrolysis, 0.2 mL of 10N KOH is added to the remaining aqueous mixture at room temperature for 15 minutes. Then the mixture is acidified and extracted with hexane/ethyl acetate (9:1). The extract is derivatized and analyzed by GC/MS as shown under Example 5.

EXAMPLE 8

Analysis of delta-9-THC in blood using d9-delta-9-THC as internal standard

An aliquot of blood (2 mL) in the test tube is treated with 2 mL of acetonitrile containing 100 ng/mL d9-delta-9-THC as internal standard. The precipitate is then centrifuged and the supernatant transferred to another tube. The residue is resuspended in 1 mL acetonitrile and then centrifuged. The supernatant is then added to the first extract and most of the acetonitrile is then evaporated under a stream of nitrogen. To the remaining aqueous mixture is added 0.2 mL of 10N KOH and the mixture extracted with hexane/ethyl acetate (9:1). The organic extract is then evaporated and the residue is derivatized using 50 μl of Nt-(butyldimethylsilyl)-N-methyl trifluoroacetamide (t-BDMS) at 70 C. for 15 minutes. The excess reagent is then evaporated under a stream of nitrogen and the residue is dissolved in 20 μl of iso-octane. The product is then analyzed using GC/MS. The following are typical conditions:

Instrument, Column and Carrier Gas: Same as Example 5;
Column Temperature: 250° C.
Ions to be Monitored: For delta-9-THC, ions at m/- 371 and 428 are monitored while ions at m/- 380 and 437 are used for d9-delta-9-THC (internal standard).

The invention has been described with reference to specific and preferred embodiments. It will be recognized by those skilled in the art that numerous changes and substitutions may be made without departing from the spirit and scope of the invention.

What is claimed is:

1. Deuterated cannabinoids having the following formula:

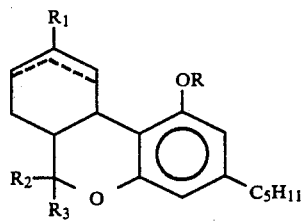

wherein R=H, alkyl having 1-8 carbon atoms or acyl of the formula $R_4CO$ wherein $R_4$ is acyl having 1-8 carbon atoms, the double bond is between the 8 and 9 positions, or between the 9 and 10 positions, and where (1) $R_1=CH_3$ and $R_2=R_3=C^2H_3$, or (2) $R_1=R_2=R_3=C^2H_3$, or (3) $R_1=CH_2OH$, $C^2H_2OH$ or $COOH$ and $R_2=R_3=C^2H_3$.

2. The compound of claim 1 wherein R=H, $R_1=CH_3$ and $R_2=R_3=C^2H_3$ and there is a double bond between the 8 and 9 positions.

3. The compound of claim 1 wherein R=H, $R_1=CH_3$ and $R_2=R_3=C^2H_3$ and there is a double bond between the 9 and 10 positions.

4. The compound of claim 1 wherein R=H, $R_1=COOH$ and $R_2=R_3=C^2H_3$ and there is a double bond between the 8 and 9 positions.

5. The compound of claim 1 wherein R=H and $R_1=R_2=R_3=C^2H_3$.

6. The compound of claim 5 wherein the double bond is between the 8 and 9 positions.

7. The compound of claim 5 wherein the double bond is between the 9 and 10 positions.

8. A composition for internal standards for analysis of cannabinoids-biological fluids consisting essentially of a deuterated cannabinoid compound selected from the deuterated cannabinoids of claim 1 in a chemically- or pharmaceutically-acceptable vehicle.

* * * * *